(12) United States Patent  
Riemenschneider et al.

(10) Patent No.: US 11,013,448 B2  
(45) Date of Patent: May 25, 2021

(54) MONITORING OF BIOSIGNALS, IN PARTICULAR ELECTROCARDIOGRAMS

(71) Applicant: Personal MedSystems GMBH, Frankfurt (DE)

(72) Inventors: Markus Riemenschneider, Limburg (DE); Jürgen Sauerzapf, Mainz (DE)

(73) Assignee: Personal MedSystems GMBH, Frankfurt (DE)

( * ) Notice: Subject to any disclaimer, the term of this patent is extended or adjusted under 35 U.S.C. 154(b) by 26 days.

(21) Appl. No.: 16/335,211

(22) PCT Filed: Sep. 26, 2017

(86) PCT No.: PCT/EP2017/074291  
§ 371 (c)(1),  
(2) Date: Mar. 20, 2019

(87) PCT Pub. No.: WO2018/060162  
PCT Pub. Date: Apr. 5, 2018

(65) Prior Publication Data  
US 2019/0350480 A1 Nov. 21, 2019

(30) Foreign Application Priority Data  
Sep. 28, 2016 (DE) .................... 10 2016 011 700.1

(51) Int. Cl.  
*A61B 5/0245* (2006.01)  
*A61B 5/08* (2006.01)  
(Continued)

(52) U.S. Cl.  
CPC ............ *A61B 5/352* (2021.01); *A61B 5/0245* (2013.01); *A61B 5/316* (2021.01); *A61B 5/366* (2021.01);  
(Continued)

(58) Field of Classification Search  
None  
See application file for complete search history.

(56) References Cited

U.S. PATENT DOCUMENTS

2004/0230105 A1 11/2004 Geva et al.  
2006/0259329 A1 11/2006 Kline  
(Continued)

FOREIGN PATENT DOCUMENTS

WO WO2003057025 7/2003  
WO WO2004032715 4/2004  
(Continued)

OTHER PUBLICATIONS

International Search Report; PCT/EP2017/074291; dated May 12, 2017.

*Primary Examiner* — Brian T Gedeon

(57) ABSTRACT

The invention relates to methods, systems and computer program products for monitoring the biosignals of a test subject, in particular electrocardiograms, wherein a plurality of reference biosignals are recorded along with a respective assigned reference parameter value, a control biosignal is measured, a reference parameter value to be assigned to the control biosignal is determined and, on the basis of the reference parameter value assigned to the control biosignal and on the basis of the plurality of reference parameter values assigned to the plurality of reference biosignals, at least one comparative biosignal is selected from the plurality of stored reference biosignals for comparison, and wherein values of the reference parameter at least partially describe a physiological state of the test subject and/or general conditions of an environment.

11 Claims, 6 Drawing Sheets

(51) Int. Cl.
*A61B 5/11* (2006.01)
*A61B 5/352* (2021.01)
*A61B 5/316* (2021.01)
*A61B 5/366* (2021.01)
*A61B 5/369* (2021.01)
*A61B 5/389* (2021.01)

(52) U.S. Cl.
CPC ............... *A61B 5/08* (2013.01); *A61B 5/1116* (2013.01); *A61B 5/1118* (2013.01); *A61B 5/369* (2021.01); *A61B 5/389* (2021.01)

(56) References Cited

U.S. PATENT DOCUMENTS

2007/0010753 A1 1/2007 MacAdam
2007/0142737 A1 6/2007 Cazares et al.

FOREIGN PATENT DOCUMENTS

WO  WO2016014194  1/2016
WO  WO2016110804  7/2016

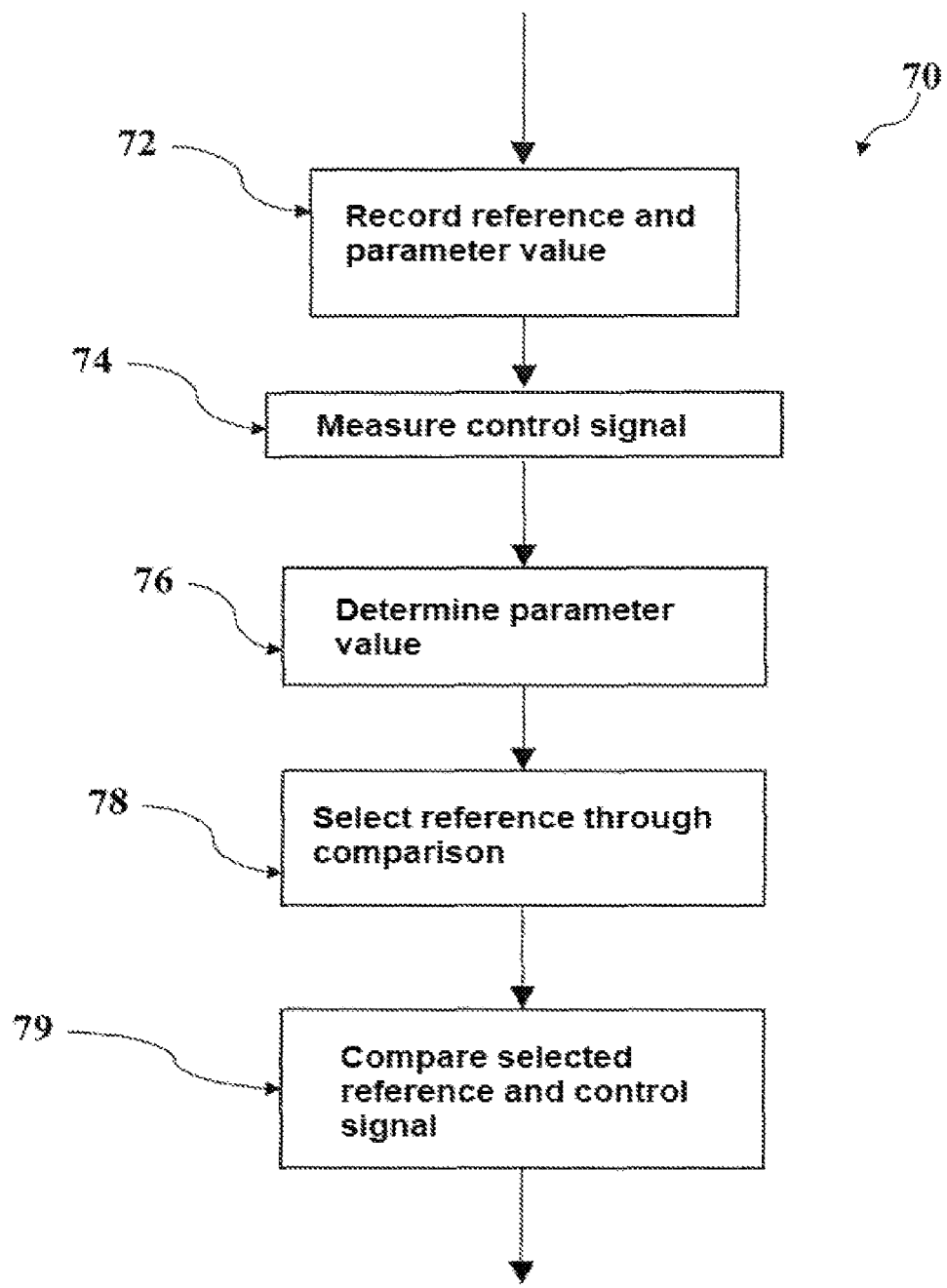

MONITORING OF BIOSIGNALS, IN PARTICULAR ELECTROCARDIOGRAMS

CROSS-REFERENCE TO RELATED APPLICATIONS

The present application is a U.S. National Stage of International Patent Application No. PCT/EP2017/074291, filed on Sep. 26, 2017, which claims priority to and the benefit of German Application No. 102016011700.1 filed in the German National Patent Office on Sep. 28, 2016, the entire contents of which are incorporated herein by reference.

TECHNICAL FIELD

The present invention relates generally to methods, systems and computer program products for monitoring biosignals, in particular electrocardiograms, and to the use of an electrocardiogram as a comparative electrocardiogram.

BACKGROUND ART

Biosignals, such as electrocardiograms, allow inferences to be drawn about the physiological activities of an organ or an organism. The evaluation of monitored biosignals is carried out not only by physicians to be used as a diagnostic basis, but is also increasingly being carried out in the area of so-called home monitoring or personal tracking.

Here, users monitor their physical activities or physiological measures without the constant support of a physician. Monitoring can form the basis for a recommendation of an action to be taken for the users, for example, an instruction to consult a physician for an in-depth diagnosis. Furthermore, monitoring may be used to evaluate or control a sports training plan, e.g. to increase stamina in marathon training.

The conspicuousness or inconspicuousness of monitored biosignals can be determined by comparison with a reference. In this case, the reference may be predetermined by a measurement of another test subject, by forming an average value over a group of test subjects or by computer-aided modeling of underlying physiological and/or pathological processes.

In this case, the reliability of the comparison (determined by the proportions of the false-positive and/or false-negative comparison results) depends, inter alia, on the quality of the reference. Furthermore, the reliability of the comparison can be increased if reference and control measurements relate to comparable conditions. These conditions include the physical conditions of the test subject and environmental influences.

From International Publication WO 96/25096, it is known to store pattern electrocardiograms for certain cardiac events of known diagnosis, e.g. tachycardia or atrial fibrillation, and compare the same with a measured electrocardiogram for a more accurate localization of disorders.

DETAILED DESCRIPTION OF THE INVENTION

Technical Problem

Having a background as mentioned above, the present invention is directed to provide improved methods, systems and computer program products for monitoring biosignals, particularly electrocardiograms. In this case, the invention relates to cases in which the determination of the measurement conditions does not require diagnosis of a pathological event, particularly a diagnosis of a cardiac event.

Technical Solution

The present invention provides a method, system, and computer program product for monitoring biosignals, particularly electrocardiograms.

In a first aspect, the present invention provides a method for monitoring biosignals of a test subject. The method includes recording a plurality of reference biosignals, particularly reference electrocardiograms, of the test subject. The plurality of reference biosignals are at least two reference biosignals. The recording may include measuring (for example, by means of a sensor) and/or interrogating (for example by reading from a memory of a plurality of reference biosignals measured at an earlier time).

In some embodiments, the biosignals may exist within a measurement curve, e.g. in a waveform over time of a measured voltage. In an electrocardiogram as an example of a measurement curve, the waveform over time of an electrical muscle activity of a heart is measured in the form of electrical potential differences.

In some embodiments, the biosignals may include measured values, e.g. voltage values or values derived from measurements. An example of biosignals that can be derived from measurement, is an ECG (electrocardiogram)-parameter well known to a person skilled in the art, such as a QT-time interval, time in a QRS-complex, ST-segment, dimensions of a P-wave/R-spike/T-wave that can be obtained from a measured electrocardiogram.

In some embodiments, the plurality of reference biosignals may exist continuously, e.g. in a multiple of points in a time series or as multiple intervals. In some embodiments, the plurality of reference biosignals may be discrete, e.g. in the form of database entries and/or one or more file(s) and/or a folder structure.

For example, a continuous time series of heart rate values should also be understood as a quantized quasi-continuous time series. Typically, heart rates can be measured at an interval of 1 heartbeat, which places a certain amount of time between two measurement points. Nevertheless, these quasi-continuous time series can be used for the purposes of the present invention, and for illustrative purposes, may be considered as being continuous. In some embodiments, a quantized series of measurements may be converted by interpolation into a strictly continuous time series.

In general, each of the plurality of reference biosignals is assigned with a respective value of a reference parameter. Values of the reference parameter describe at least partially a physiological state of a test subject and/or a boundary condition of surroundings. In particular, a reference parameter can influence biosignals. In general, a reference parameter (or a determination of a value of a reference parameter) does not require a diagnosis of a pathological event, particularly a cardiac event. For example, according to the present invention, the presence or absence of a pathological diagnosis (e.g., a cardiac arrhythmia) should not be used as a reference parameter for selecting a comparative biosignal (e.g., a comparative electrocardiogram).

In some embodiments, the reference parameter may take on numerical values, optionally in conjunction with a unit. An example of a reference parameter is a heart rate, which may be expressed in units of "beats per minute". The numerical value can assume integer and/or floating point values depending on the reference parameter. In some embodiments, the reference parameter may take on descriptive values. An example of a reference parameter with descriptive values is posture, with values such as "lying down", "sitting", and "standing".

Examples of reference parameters whose values at least partially describe a physiological state of a test subject are as follows:

heart rate, ECG-parameters that can be determined from an electrocardiogram (e.g., QT-time interval, times and/or amplitudes in a QRS-complex, ST-segment, P-wave, R-spike, T-wave, Q-spike, S-spike, U-wave, zero-line), blood sugar level, blood pressure, oxygen content in blood (SpO2), electrolyte levels (e.g., concentration of calcium, potassium, sodium), body temperature, respiratory rate, minute ventilation;

these examples of reference parameters may be indicated by numerical values, optionally in conjunction with a respective matching unit.

Further examples of reference parameters whose values at least partially describe physiological states of the test subject are:

medication of the test subject; posture of the test subject, current and/or motion state of the test subject up till now; habits of the test subject, particularly occupation, eating habits, frequency of sports activity thereof.

These further examples of reference parameters may be indicated by descriptive values, optionally numerically or binary coded. Therefore, a reference parameter "medication of the test subject" may take on, for example, "yes", "no", "amiodarone yes", "amiodarone no" or a plurality of values to be determined depending on the test subject and/or the biosignals to be monitored. A reference parameter "motion state" may take on descriptive values, such as "relax"; "sports activity", "running", "was running till now"; "load on the ergometer", etc.

Examples of reference parameters whose values at least partially describe boundary conditions of the surroundings of a test subject are:

time of day, ambient temperature, air pressure, humidity, season.

The above-described examples of reference parameters are intended to be illustrative and not to be construed as a limiting enumeration. Reference parameters other than those mentioned are also included as long as they can affect biosignals.

In some embodiments, a reference parameter may include a plurality of components. In such cases a multi-component reference parameter or of a reference parameter consisting of a set of a plurality of components may be mentioned. For example, the components "heart rate" and "posture" may form a set "(heart rate; posture)" as a reference parameter. Values of a multi-component reference parameter are determined by the values of its components. Therefore, as an example, "62 beats per minute; lying down" may be a possible value of a reference parameter "(heart rate; posture)", where "62 beats per minute" is a possible value of the component "heart rate" and "lying down" is a possible value of the component "posture". A set of n number of components can be represented mathematically as n-tuples, and in other words, can be represented wherein the order of the components is not negligible. In some embodiments, the components may each be weighted differently.

The method further comprises measuring a control biosignal of a test subject, particularly a control electrocardiogram, and determining a value of a reference parameter assigned to the control biosignal. The determining may include a measurement, an automatic recognition or an input by the user. Preferably, the assignment of the control biosignal and the determined value is carried out on the basis of a temporal proximity or even simultaneity of measurement of the control biosignal and determination of the value of the reference parameter.

The method further comprises selecting at least one comparative biosignal, particularly at least one comparative electrocardiogram, from a plurality of stored reference biosignals, based on a value of a reference parameter assigned to a control biosignal, and on a plurality of values of a reference parameter assigned to a plurality of reference biosignals. Preferably, a single comparative biosignal is selected.

In some embodiments, among the plurality of reference biosignals, a reference biosignal having an assigned value of a reference parameter representing a value identical to or having the smallest difference with respect to a value of the reference parameter assigned to the control biosignal is selected as the comparative biosignal.

In some embodiments, among a plurality of reference biosignals, a reference biosignal having an assigned value of a reference parameter representing the next higher or the next lower value with respect to a value of a reference parameter assigned to a control biosignal is selected as the comparative biosignal.

In some embodiments, especially in the case of a multi-component reference parameter, a standard may be defined for the purpose of comparing multi-component values of the reference parameter. As an illustrative example, the set "(heart rate; blood sugar level)" may be mentioned as a multi-component reference parameter: a question may arise as to whether a control value of (65 bpm; 105 mg/dl) would be "closer" to (60 bpm; 90 mg/dl) or (70 bpm; 110 mg/dl). To settle such a question, a standard may be formed for each multi-component set. For example, a Euclidean standard (weighted and/or taking units into account) or a conditional standard may be formed. For example, a conditional standard may dictate in advance that at first, only the first mentioned parameter (in the example: heart rate) should be considered and only in the case of an ambiguous result (as in the example identical difference of 5 bpm) the second mentioned parameter (in the example: blood sugar level) should be cited as a reference. In the example mentioned, in the case of this conditional standard, the value (70 bpm, 110 mg/dl) would be selected. As an alternative standard, a Euclidean standard in the above-mentioned case can represent the numerical values of heart rate in the bpm unit and blood sugar level in the mg/dl unit in a (optionally weighted) Euclidean coordinate system, and the difference can be defined as the length of the difference vector.

In general, the method further includes comparing the measured control biosignal with the selected comparative biosignal. The comparison of the biosignals may additionally or alternatively include particularly the comparison of values derived from the biosignals to be compared. For example, to compare two electrocardiograms, one or more of common ECG-parameters (amplitudes, time waveforms, rhythm parameters, QT-time interval, times in the QRS-complex, ST-segment, sizes of the P-wave/R-spike/T-wave) are compared.

In general, for example, the reference biosignals can be regarded as being inconspicuous or conspicuous at the time of their recording, measurement or interrogation. In some embodiments, for example, reference biosignals recorded on a healthy test subject may be considered as being inconspicuous. In the case where a reference biosignal is classified as being inconspicuous, a negative comparison result (that is, a mismatch of the control signal and reference signal)

may lead to an instruction to visit a physician. In the case where a reference biosignal is classified as being conspicuous, a positive comparison result (that is, matching control and reference signals) may lead to an instruction to visit a physician.

In some embodiments, certain requirements for data quality of reference biosignals may be imposed, such as a high signal-to-noise ratio. Biosignals that meet such requirements may be considered suitable for comparison.

In some embodiments, a measured control biosignal may be recorded by the amount of a plurality of reference biosignals. The value of a reference parameter assigned to the measured control biosignal can be assigned to a newly recorded reference biosignal. Thus, the amount of reference biosignals in operation for future process executions may be further increased, and it is possible to cover a wider or finer resolved spectrum of values of the reference parameter. Such a recording can be particularly preferable if the measured control biosignal is regarded as being inconspicuous.

In some embodiments, the method may further include outputting or displaying information. Examples of information to be output are: a value of a reference parameter assigned to a control biosignal; a value of a reference parameter assigned to a selected comparative biosignal; the control biosignal; the comparative biosignal; a deviation between the control biosignal and the comparative biosignal; a deviation between the value of the reference parameter assigned to the control biosignal and the value of the reference parameter assigned to the selected comparative biosignal; an action recommendation based on a deviation between the control biosignal and the comparative biosignal. The action recommendation to be output may, for example, be directed to having a test subject sit down, relax or record a sports activity.

The output can be made, for example, optically, acoustically, tactually or in a combination of the same.

Biosignals to be monitored may generally allow inferences to be drawn about the activities of organs of a test subject or an organism. Determination of any location of a diagnosis based on the monitored biosignals, that is, the determination of a disease by a physician is not a part of the method according to the present invention.

Examples of biosignals to be monitored are blood pressure curves, hemograms, electrocardiograms, electroencephalograms, electromyograms, electroretinograms. Alternatively or additionally, records of the composition of respiratory gas (e.g., $CO_2$-fraction determined by capnometry) or excretion (e.g., urine composition determined by urine test strips) may serve as biosignals.

The measurement of biosignals can be carried out, for example, by means of suitable sensors, in particular electrically, as in the case of electrocardiograms. Preferably, the measurement is carried out in a non-invasive manner.

In some embodiments, a plurality of control biosignals, particularly a plurality of control electrocardiograms, may be measured. For example, the plurality of control biosignals may be measured as a time series. Such a method of measurement may be particularly preferred in long-term monitoring, such as a long-term ECG.

In particular, for example, since a reference parameter does not change significantly over time, a single value of the reference parameter may be determined for a plurality of control biosignals. In such cases, among the plurality of reference biosignals, only one is selected as a comparative biosignal and compared with each of the plurality of control biosignals.

Alternatively, for example, since values of a reference parameter change over time, a respective value of the reference parameter may be determined for each of the plurality of control biosignals. In such cases, a respective comparative biosignal is selected from the plurality of reference biosignals for each control biosignal and compared with the respective control biosignal.

In a second aspect, the present invention provides a computer program product that is stored on a computer readable medium and performs the steps of the method of the present invention using a program code implemented by a computer.

In a third aspect, the present invention provides a system for monitoring biosignals of a test subject. The system includes at least one sensor, a memory and a controller.

The at least one sensor is designed to measure a control biosignal of a test subject. In particular, the at least one sensor may be ECG-electrodes for measuring electrocardiograms. In some embodiments, the at least one sensor may be connected to components of the system, particularly in a state connected to a cable and the controller (e.g., via a USB interface) or in a state connected without the cable (e.g., via a Bluetooth interface) or may be configured to be connected. In some embodiments, the at least one sensor may be arranged together with at least the controller in or on a common housing.

In some embodiments, the at least one sensor may be further configured to measure a plurality of reference biosignals of a test subject.

The memory is designed to store a plurality of reference biosignals, particularly reference electrocardiograms, of a test subject. Each of the plurality of reference biosignals is assigned with a respective value of a reference parameter. The assigned values of the reference parameter may also be stored in the memory. In some embodiments, the memory may be located remotely, for example, on a server or in a decentralized network.

The controller is configured to determine a value of a reference parameter assigned to a control biosignal. Preferably, the determination of this value can be carried out automatically, for example by measurement by at least one sensor or by another sensor, or manually, for example by user input in an input interface.

Furthermore, the controller is configured to select at least one comparative biosignal, particularly at least one comparative electrocardiogram, from a plurality of stored reference biosignals, based on a determined value of a reference parameter and on a plurality of values of the reference parameter assigned to a plurality of reference biosignals.

Further, the controller is configured to compare the control biosignal and the comparative biosignal.

In a fourth aspect, the present invention provides the usage of an electrocardiogram as a comparative electrocardiogram with respect to a control electrocardiogram. The electrocardiogram was selected from a plurality of reference electrocardiograms. A respective value of the reference parameter is assigned to each of the plurality of reference electrocardiograms and the control electrocardiogram. The selection of the electrocardiogram is based on the assigned values of the reference parameter.

BRIEF DESCRIPTION OF THE DRAWINGS

Exemplary embodiments of the present invention will now be described by way of example and with reference to the following drawings.

FIG. 7 illustrates a flowchart of a method according to the present invention.

DETAILED DESCRIPTION OF THE EMBODIMENTS

The following embodiments exemplify cases of biosignals in the form of electrocardiograms. Electrocardiograms map electrical activities of the heart in the form of temporal voltage waveforms, which can be measured by, for example, ECG-electrodes on the body of a test subject.

Figure 1A:
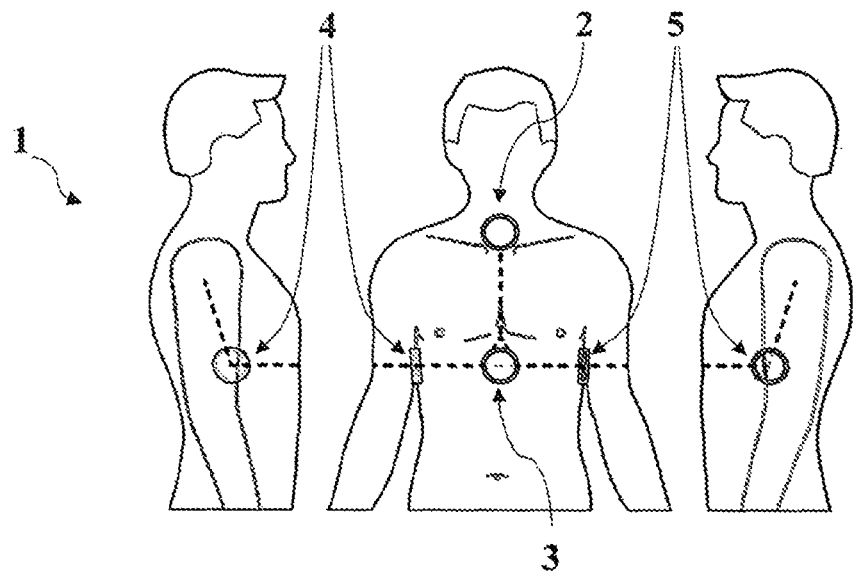
FIG. 1A illustrates a human torso with sensors for measuring electrocardiograms.

FIG. 1A illustrates three views of a human torso 1 of a test subject with four ECG-electrodes 2 to 5. Each of the four electrodes are attached to, an upper end of the sternum (electrode 2), a lower end of the sternum (electrode 3), a right side along a middle axis line at a height of the lower sternum margin (corresponding to the height of the electrode 3) (electrode 4) and a left side along the middle axis line at the height of the lower sternum margin (corresponding to the height of the electrode 3) (electrode 5). Other sensor arrangements for measuring electrocardiograms with a different number of ECG-electrodes, for example ten electrodes, are known and can also be used for the purposes of the present invention, particularly for the measurement of electrocardiograms. For example, the electrodes 2 to 5 may be configured as adhesive disposable electrodes and may include a wet gel or dry gel.

Depending on the arrangement of the electrodes, the existing electrodes are connected in such a way that certain discharges or channels are obtained. The four electrodes 2 to 5 illustrated in FIG. 1A make it possible, for example according to the EASI method, to calculate a 12-channel-ECG recorded as a derivative according to Einthoven (I, II, III), Goldberger (aVR, aVL, aVF) and Wilson (V1 to V6). Alternatively or additionally, the extended chest wall derivative (V7 to V9 and VR3 to VR9) and/or an ECG-mapping can be calculated. Other interconnection methods and/or derivatives (e.g., derivatives of Einthoven, Goldberger, Wilson, Nehb, Franck, or Dower) are also suitable for measuring electrocardiograms for the purpose of the present invention.

For purposes of illustration, reference is made in the course of the description to, for example, a 12-channel-ECG recorded using four electrodes 2 to 5. However, the present teaching can also be implemented some other than 12-channel ECGs, particularly implemented with vector-ECGs or with 1-channel-ECGs, or with other biosignals.

Figure 1B:
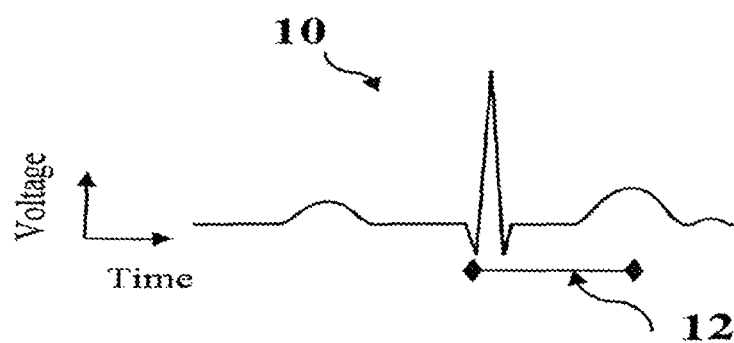
FIG. 1B illustrates a schematic view of two measured electrocardiograms.

FIG. 1B is a schematic view of two measured electrocardiograms 10 and 14 of a test subject. Each electrocardiogram is illustrated here as a waveform over time of an electrical voltage over duration of approximately one heartbeat. The illustrated electrocardiograms 10 and 14 are derivatives according to Einthoven II.

For the purpose of the present invention, the term "electrocardiogram" may illustrate a single waveform over time for a single derivative, e.g. a derivative according to Einthoven II, or may illustrate a plurality of waveforms over time for various derivatives. Therefore, in particular, the entirety of twelve graphs of a 12-channel-ECG can also be referred to as an "electrocardiogram".

For purposes of illustration, each electrocardiogram will hereinafter be represented by a graph, e.g. a derivative according to Einthoven II.

The electrocardiogram 10 is a schematic view of a physiological electrocardiogram of a test subject in a healthy state. The electrocardiogram was recorded as a so-called relaxing ECG, when the test subject was in a relaxing state. It can be referred to as reference electrocardiogram 10.

From the measured electrocardiogram, well known ECG-parameters, such as a QT-time interval, times in the QRS-complex, ST-segment, sizes of the P-wave, R-spike, T-wave, can be determined. Hereinafter, as an example, the QT-time interval, that is, the temporal interval of a Q-spike (a first negative rash in the QRS-complex caused by chamber stimulation) and T-wave (repolarization towards an end of the ECG-waveform) is discussed. The QT-time interval of the electrocardiogram 10 is schematically emphasized by duration 12.

Likewise, as shown in FIG. 1B, the electrocardiogram 14 was recorded later than the electrocardiogram 10. It was recorded for the same test subject as electrocardiogram 10. In particular, compared to the reference electrocardiogram 10 classified as being inconspicuous, the monitoring or control of heart activity can be recorded. The electrocardiogram 14 that is recorded later is referred to as the control electrocardiogram 14. Here, the control electrocardiogram 14 has an increased QT-time interval with respect to the reference electrocardiogram 10. The control electrocardiogram 14 may therefore be regarded as being conspicuous with respect to the reference electrocardiogram 10.

A change in the QT-time interval can have a variety of causes. For example, an increase in heart rate may result in a decrease in QT-time. Medication, e.g. the administration of amiodarone may also lead to an extension of QT-time. There is also a correlation between certain electrolyte concentrations in the blood and changes in QT-time. For example, hypercalcemia or hyperkalemia may be associated with reductions in QT-time. However, a long QT-time may also be an indicator of certain arrhythmias, such as bradycardia.

Thus, on the basis of a comparison of the reference electrocardiogram 10 and the control cardiogram 14, there is an uncertainty as to which of the influencing factors referred to is the cause for the change in the QT-time interval determined in the comparison process.

Figure 2:
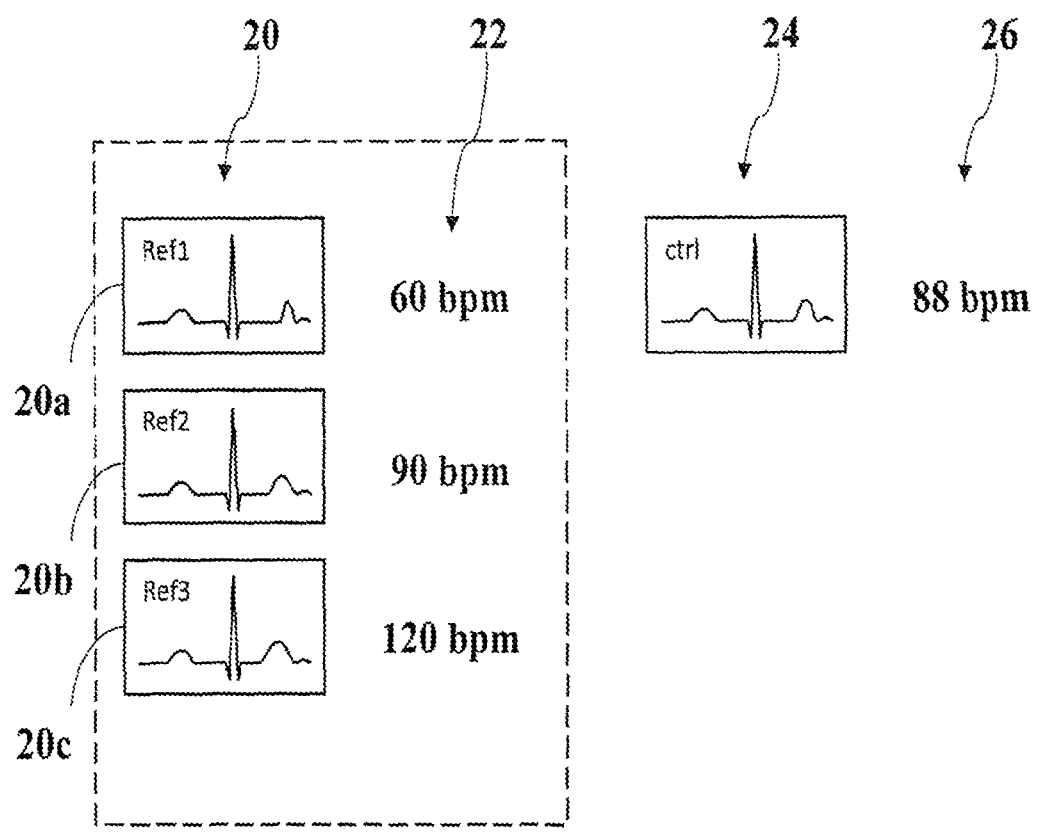
FIG. 2 illustrates three reference electrocardiograms with assigned values of a reference parameter "heart rate", as well as a control electrocardiogram with an assigned value of the reference parameter "heart rate" according to an embodiment.

In FIG. 2, values of a reference parameter and electrocardiograms from a method according to the present invention for monitoring biosignals of a test subject are illustrated schematically.

Meanwhile, there are a plurality of reference electrocardiograms 20 of the test subject with a plurality of heart rate values 22. In this case, for each of the plurality of reference electrocardiograms 20, respective heart rate values are assigned. The respective assigned value corresponds to the heart rate at which the respective reference electrocardiogram was measured. With this, here there is assigned an electrocardiogram value of, for example, 60 beats per minute (in bpm (beats per minute) unit) to a first reference electrocardiogram. Alternatively, a heart rate value may be indicated in another unit, e.g. in hertz, where 1 Hz corresponds to a heart rate of 60 beats per minute. Furthermore, a reference parameter "RR-interval", that is, the interval of the R-spikes over time in the electrocardiogram of two consecutive cardiac cycles (for example, expressed in milliseconds) corresponds to a heart rate. The second reference electrocardiogram 20b and third reference electrocardiogram are assigned heart rate values of 90 bpm and 120 bpm, respectively.

In the embodiment illustrated here, a set of a plurality of reference electrocardiograms 20 is configured to have three electrocardiograms 20a to 20c. In general, the set of reference electrocardiograms may consist of two or more electrocardiograms. By increasing the number of reference electrocardiograms, the covered spectrum of reference parameter values can be widened, for example to cover not only the range between 60 bpm and 120 bpm, but also lower heart rates, such as 50 bpm, and/or higher heart rates, such as 150 bpm.

Alternatively or additionally, by increasing the number of reference electrocardiograms, the resolution within the covered spectrum can be increased. Thus, instead of the intervals between heart rate values of 30 bpm present here in the illustrated embodiment, comparatively lower intervals, e.g. of 15, 10, 5 or 1 bpm can be obtained. This allows a more accurate or reliable monitoring of the electrocardiograms to be achieved.

In the present case, the plurality of reference electrocardiograms 20 differ particularly by the position and shape of the T-wave, that is, the repolarization at the right end of the electrocardiogram. Accordingly, the plurality of reference electrocardiograms has different QT-times. The QT-time is greater in the first reference electrocardiogram 20a than in the other two reference electrocardiograms 20b and 20c. The QT-time at the third reference electrocardiogram 20c is lower than in the reference electrocardiograms 20a and 20b. Such a situation is consistent with the QT-time physiologically decreasing along with increasing heart rate. The plurality of reference electrocardiograms were measured for a healthy test subject.

Furthermore, there is a control electrocardiogram 24 of the test subject having an assigned heart rate value 26 of 88 bpm. The control electrocardiogram 24 was measured on the same test subject at a later time to monitor cardiac function. In conjunction with the measurement of the control electrocardiogram 24, the heart rate value 26 was also determined.

In a method according to the present invention, the control electrocardiogram 24 can be compared with at least one of the plurality of reference electrocardiograms 20. For this purpose, a comparative electrocardiogram is selected from the plurality of reference electrocardiograms 20. Such a selection is based on a plurality of heart rate values 22 assigned to the reference electrocardiograms 20 and on the heart rate value 26 assigned to the control electrocardiogram 24. Preferably, among the plurality of reference electrocardiograms 20, the one of which an assigned heart rate value 22 has the smallest difference with respect to the heart rate value 26 (assigned to the control electrocardiogram) may be selected as a comparative electrocardiogram (the difference being expressed as an absolute value). Here, the second reference electrocardiogram 20b has a difference of 2 bpm, whereas the reference electrocardiograms 20a and 20c have differences of 28 bpm and 32 bpm respectively with respect to the heart rate 26 of the control electrocardiogram 24. Consequently, the second reference electrocardiogram 20b has the smallest difference in heart rate. The second reference electrocardiogram 20b is selected as the comparative electrocardiogram for comparison with the control electrocardiogram 24. In other embodiments, among the plurality of reference electrocardiograms 20, the one of which an assigned heart rate 22 represents the next lower or the next higher value with respect to the heart rate value 26 (assigned to the control electrocardiogram 24) may be selected as a comparative electrocardiogram. When illustrated, this is the first reference electrocardiogram 20a or the second reference electrocardiogram 20b.

In the present case, the control electrocardiogram doesn't have any changes in change of QT-time or any other significant changes for the comparative electrocardiogram 20b. Therefore, the control electrocardiogram can be classified as being inconspicuous with respect to the comparative electrocardiogram.

For example, in a method for monitoring electrocardiograms that does not follow the present invention, where there are no plurality of reference electrocardiograms, a control electrocardiogram would be compared to a single reference electrocardiogram available, measured for example as an electrocardiogram 20a at a heart rate of 60 bpm. In this case, a deviation of the QT-time would be determined, but deducing the cause (e.g., physiological frequency dependence or pathological cause) would be impossible. Nevertheless, when a diagnosis is made based on the deviation, the risk of false-positive results particularly increases. When information about the underlying heart rate (e.g 60 bpm) is included in the only available reference electrocardiogram, at least one frequency-dependent matching of the QT-time parameter would be possible. However, such a matching may be based on, for example, a mathematical or statistical model wherein exact conditions of the individuals can only be considered in an incomplete manner. Examples of frequency-dependent adjustments of the QT-time are the Hegglin formula, Bazett formula or the Fridericia formula. The changes in the electrocardiogram may vary for each test subject and therefore cannot be generalized.

In comparison, in some embodiments of the invention, particularly when the difference in the heart rate values is small, as in the case illustrated in FIG. 2, a frequency-dependent matching of the QT-time parameter is unnecessary.

Figure 3A:
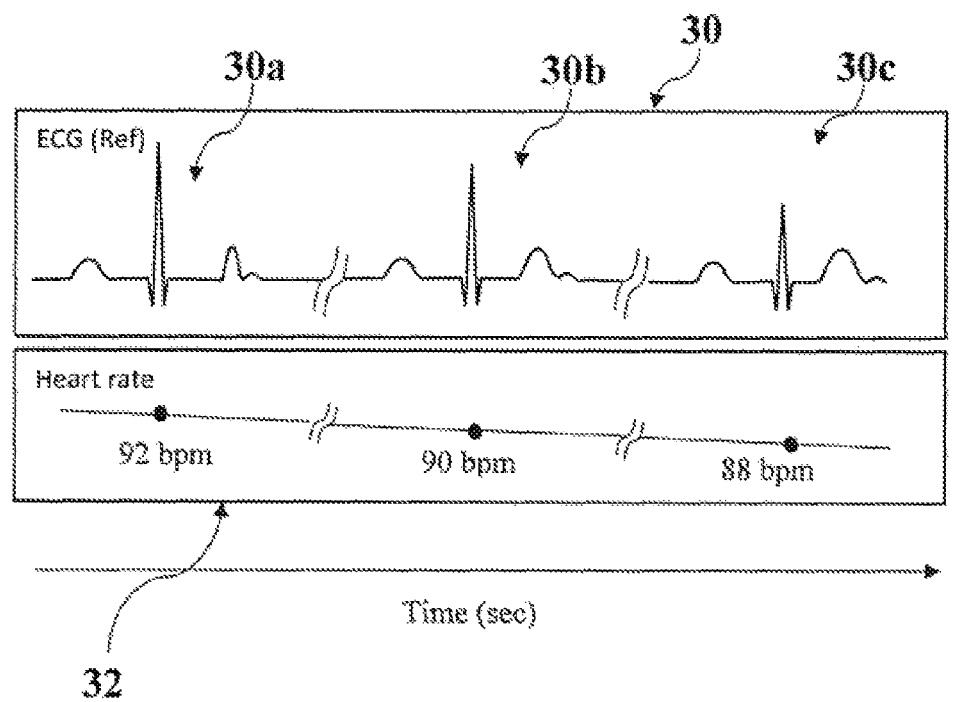
FIG. 3A illustrates three reference electrocardiograms with assigned values of a reference parameter "heart rate" according to another embodiment.

In FIG. 3, electrocardiograms and values of a reference parameter, as may be present in the course of another embodiment of a method according to the invention for monitoring biosignals of a test subject, are schematically illustrated. FIG. 3A illustrates a plurality of reference electrocardiograms 30 and a plurality of heart rate values 32 as reference parameters.

The plurality of reference electrocardiograms 30 of the test subject are measured as a continuous time series. The plurality of heart rate values 32 are also measured simultaneously to or in synchronized with the plurality of reference electrocardiograms as a continuous time series. The illustrated waveforms of the heart rates are based on an interpolation, which converts a quasi-continuous series of measurements by means of data processing into a strictly continuous time series.

The plurality of heart rate values 32 are assigned to the plurality of reference electrocardiograms 30 by means of the synchronized recording and a common time axis due to the synchronized recording.

The plurality of reference electrocardiograms 30 and the plurality of heart rate values 32 of the embodiment as shown in FIG. 3A, for example, can be measured as a result of stimuli that increases the heart rate, such as intended stress of the test subject on an ergometer. The test subject has (for example, by the system according to the present invention) received an instruction to spend energy until reaching maximum stress on the ergometer or over a defined period of time. Immediately after the stress is over, the heart rate of the test subject is at a maximum. Other forms of stress for the initial increase in heart rate are repeating stair climbing or squats a certain number of times. Additionally or alternatively, the heart rate can be increased by medication.

After reaching a maximum heart rate and physical stress is over, the measurement of reference electrocardiograms was started. At the same time the heart rate was recorded. The heart rate can be recorded directly from the reference electrocardiograms, by means of RR-intervals. Thus, no additional sensor devices (e.g., pulsometer) are necessary. Furthermore, the synchronization of the two time series is facilitated by the direct determination of the time series of the measured reference electrocardiograms.

Over time, the heart rate slowly decreases from the maximum to a relaxing pulse. In this embodiment, a wide spectrum of heart rates from the maximum pulse to the relaxing pulse can be recorded. Depending on the rate of decrease in heart rate, it may be possible to record reference electrocardiograms in all integer heart rates within the covered range and assign to such reference electrocardiograms. In such cases, identity of heart rate values may be required for later selection for comparison with a control electrocardiogram. For illustration purposes, only a portion of the time series is shown in FIG. 3A, namely three areas at about 90 beats per minute. A heart rate of 92 bpm is assigned to the reference electrocardiogram 30a. A heart rate of 90 bpm is assigned to the reference electrocardiogram 30b. A heart rate of 88 bpm is assigned to the reference electrocardiogram 30c.

Alternatively or additionally, in some embodiments, the measurement of reference electrocardiograms may be performed during heart rate rise, e.g., during stress on an ergometer.

Figure 3B:
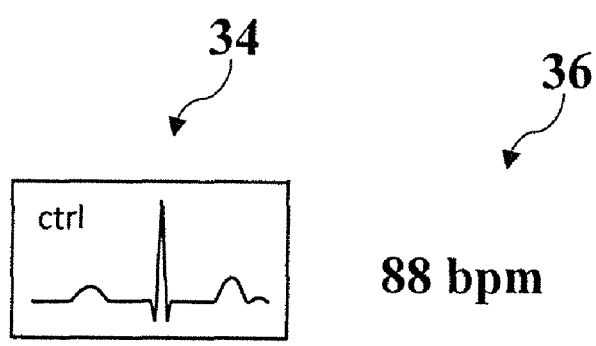
FIG. 3B illustrates a control electrocardiogram with an assigned value of a reference parameter "heart rate" according to the embodiment of FIG. 3A.

In FIG. 3B, a control electrocardiogram 34 is illustrated, which was measured on the same test subject at a later time for monitoring. At the same time, a heart rate value 36 of 88 beats per minute is determined and assigned to the control electrocardiogram 34.

By comparison, among the plurality of heart rate values 32, the heart rate value identical to or having the smallest difference with the heart rate value 36 is determined. In the case of the illustrated embodiment, the reference electrocardiogram 30c and the control electrocardiogram 34 are assigned with identical heart rate values, namely 88 beats per minute. The reference electrocardiogram 30c is selected as a comparative electrocardiogram and compared to the control electrocardiogram 34.

This allows effective monitoring of a test subject, particularly an athlete during training or a convalescent during rehabilitation: the heart rate changes in the range of stress-ECG. According to the teaching of the present invention, particularly in the exemplary embodiment illustrated here, it is possible to select a suitable reference electrocardiogram for each control electrocardiogram in the course of the stress-ECG and more specifically, to select a reference electrocardiogram measured under the same or similar conditions.

Thus, stress-induced changes in the ECG curve can be differentiated from changes by other causes (e.g., pathological causes such as circulatory disturbance).

In the case where two of the plurality of heart rate values 32 have the same difference to that of heart rate value 36, both of the assigned electrocardiograms can be selected as comparative electrocardiograms and used for comparison. Alternatively, a mean comparative electrocardiogram may be formed from the two selected reference electrocardiograms. Further alternatively, one of the two reference electrocardiograms (for example: the reference electrocardiogram having a lower/a higher assigned value of the reference parameter; or the more recent reference electrocardiogram with different recording data) may be selected as a comparative electrocardiogram in a random or predetermined manner.

Figure 4:
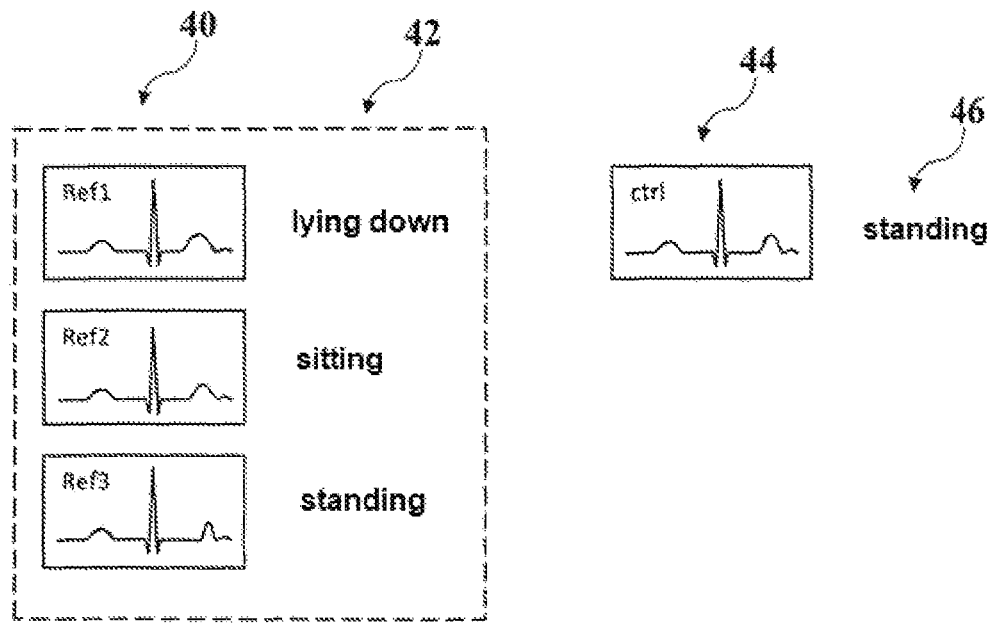
FIG. 4 illustrates three reference electrocardiograms and a control electrocardiogram with respectively assigned values of a reference parameter "posture".

In FIG. 4, three reference electrocardiograms 40 of a test subject with assigned values 42 of the reference parameter "posture", as well as a control electrocardiogram 44 of the same test subject with an assigned value 46 of the reference parameter "posture" are illustrated schematically.

The reference parameter, "posture", is a reference parameter that assumes non-numerical values. In a computer-based implementation, each of these non-numerical values can be assigned with a numeric value or binary value corresponding to a coding. By way of illustration, the values are illustrated here in their descriptive word form. Here, the reference parameter "posture" assumes the values of, for example, lying down, sitting or standing.

The reference parameter "posture" influences the form of electrocardiograms by means of the so-called location type, as explained below. Electrocardiograms can be considered as projections of a dipole in a test subject's body using the various derivatives above. In the case where the position of an electrode is given, e.g., as shown in FIG. 1A, a measured electrocardiogram depends inter alia on the orientation of the dipole to be projected. The term of orientation is commonly described as, for example, a location type associated with a hex-axial reference system. Examples of location types include a standard type, left type and right type. In an example of the derivative of Einthoven I (between the left and right arm) a strong positive R-spike is shown in the left type, whereas the R-spike (in the derivative according to Einthoven I) can even be negative for a right type. Corresponding location type dependent changes can also be found in other derivatives and other characteristics of the electrocardiogram (shape of the P-wave, T-wave, etc.). Changes in the location type may have pathological causes, e.g. such as hypertrophy. For example, a left ventricular hypertrophy (LVH) causes a shift from standard type to a left type. At the same time, however, the posture has an influence on the location type. Getting up can cause changes in the electrocardiogram that resemble a right type. Therefore, the comparison of electrocardiograms measured in different postures, can be wrong or lead to unfounded comparison results. In particular, in long-term ECG examinations, situations may occur wherein the test subject changes his/her posture during the course of measurement.

Therefore, in the exemplary embodiment of FIG. 4, one of the reference electrocardiograms 40 is selected for comparison with the control electrocardiogram, whose assigned posture value 42 coincides with that of the control electrocardiogram 44 (i.e., "standing"). Thus it is avoided that electrocardiograms measured in different postures (and therefore having a different type of posture) are compared.

Figure 5:
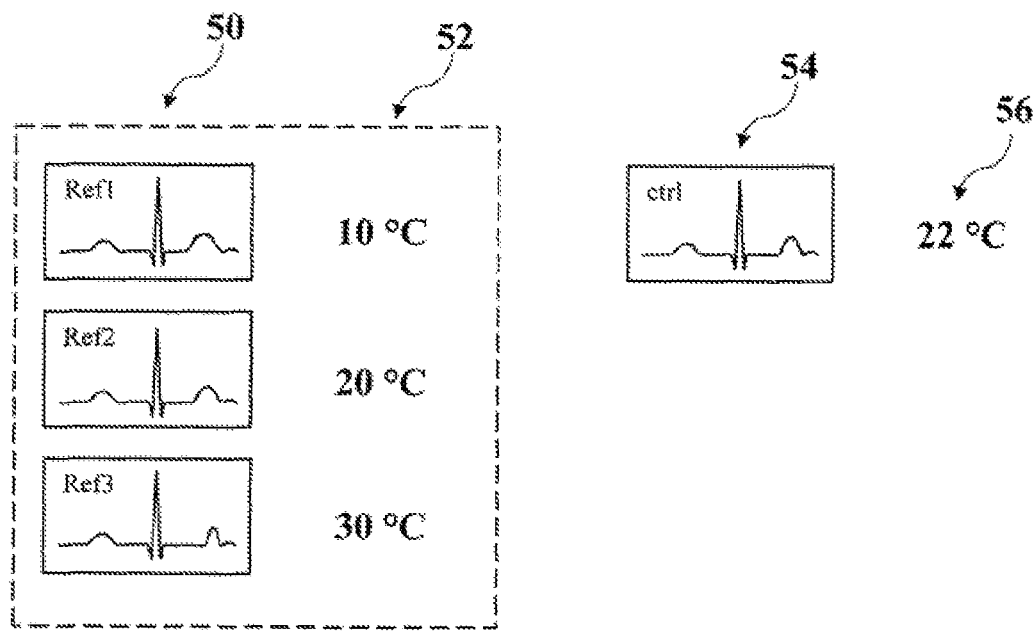
FIG. 5 illustrates three reference electrocardiograms and a control electrocardiogram with respectively assigned values of a reference parameter "ambient temperature".

FIG. 5 illustrates three measured reference electrocardiograms 50 of a test subject with assigned values 52 of the reference parameter "ambient temperature", as well as a measured control electrocardiogram 54 of the test subject with an assigned value 56 of the reference parameter "ambient temperature".

Values of the reference parameter "ambient temperature" at least partially describe boundary conditions of the surroundings or environment of the test subject during the measurement.

Based on an ambient temperature value 56 assigned to the control electrocardiogram 54 and on a plurality of ambient temperature values 52 assigned to a plurality of reference electrocardiograms 50, a comparative electrocardiogram may be selected. In the present case where the ambient temperature value 56 is 22° C., the closest value among the values 52 of the reference electrocardiograms 50 is the ambient temperature of 20° C. This ambient temperature is assigned to a second reference electrocardiogram among the three reference electrocardiograms 50. This second reference electrocardiogram 50 is selected as a comparative electrocardiogram and compared with the control electrocardiogram 56. Thus, a situation of having electrocardiograms, which were measured under different boundary conditions of surroundings, are compared can be avoided.

Figure 6:
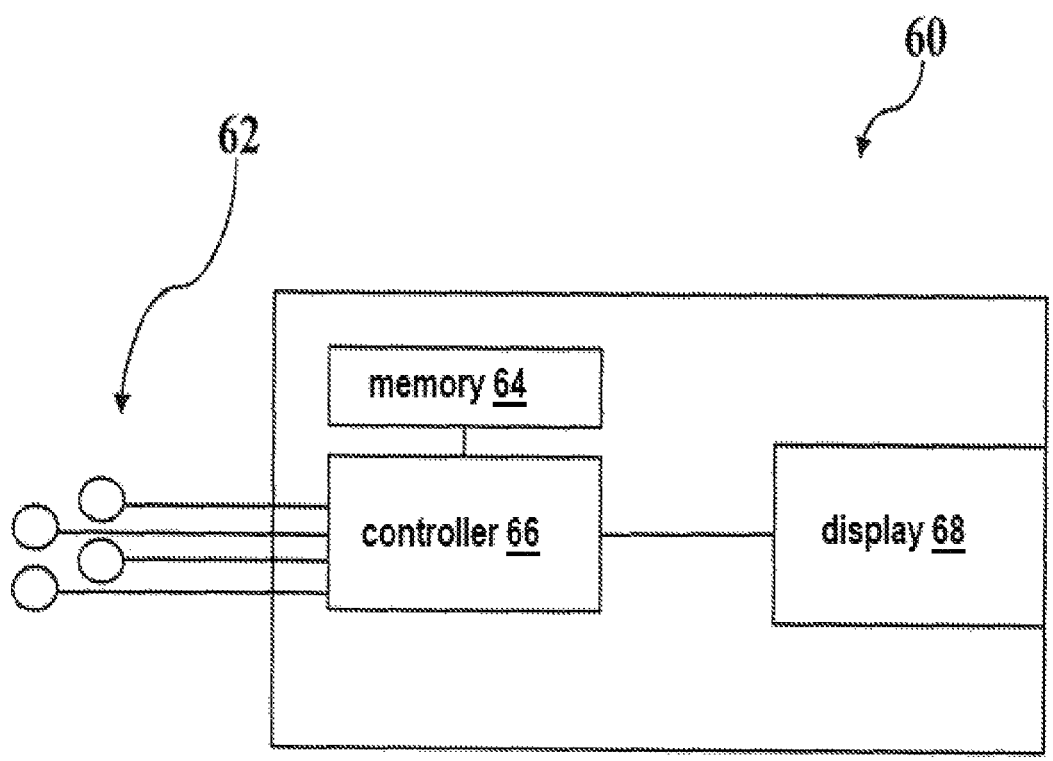
FIG. 6 illustrates an embodiment of a system according to the present invention.

FIG. 6 illustrates an embodiment of a system 60 for monitoring electrocardiograms of a test subject with four sensors 62, a memory 64, a controller 66 and a display 68.

Figure 1B:
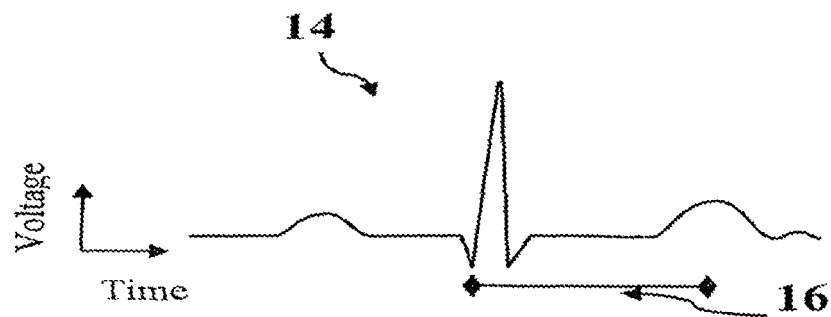

The sensors 62 are formed as ECG-electrodes and designed to measure a control electrocardiogram. For this purpose, they can be arranged particularly according to FIG. 1 on the test subject. Further, the sensors 62 are configured to measure a plurality of reference electrocardiograms.

The memory 64 is configured to store the plurality of reference electrocardiograms. In the memory, each of the plurality of reference biosignals is assigned with a respective value of a reference parameter. The storage and assignment of reference electrocardiograms and reference parameter values can be performed, for example, in a database format.

The controller 66 is configured to determine a value of a reference parameter to be assigned to a control electrocardiogram. Here, the determination of the value of the reference parameter comprises measurement by means of the sensors 62.

Further, the controller 66 is configured to select a comparative electrocardiogram, from the plurality of stored reference electrocardiograms, based on a certain value of the reference parameter assigned to the control electrocardiogram and the plurality of values of the reference parameter assigned to the plurality of reference electrocardiograms.

Further, the controller 66 is configured to compare the control electrocardiogram and the comparative electrocardiogram.

The display 68 is configured to output information. The display 68 is configured as an LCD screen to optically output the information. In particular, it is designed to output whether a method for monitoring electrocardiograms could be properly performed. Furthermore, it is configured to properly execute the method and then issue an action recommendation based on the comparison between the control electrocardiogram and comparative electrocardiogram. For example, an action recommendation to be issued may be directed to sitting down, relaxing or recording a sports activity of the test subject.

FIG. 7 illustrates a flow chart of a method 70 according to an embodiment. The method 70 is used for monitoring biosignals of a test subject.

The method includes, recording 72 a plurality of reference biosignals having respective reference parameter values of the test subject, measuring 74 a control biosignal of the test subject, determining 76 a value of the reference parameter, selecting 78 a comparative biosignal from the plurality of stored reference biosignals and comparing 79 the measured control biosignal with the selected comparative biosignal.

Selecting 78 a comparative biosignal from the plurality of recorded reference biosignals is based on the certain value of the reference parameter determined in step 76 and on the plurality of values of the recorded reference parameter in step 72.

Values of the reference parameter at least partially describe physiological states of the test subject and/or boundary conditions of an environment and do not require a diagnosis of a pathological event, particularly a cardiac event.

The invention claimed is:

1. A method for monitoring biosignals of a test subject, comprising:
 recording a plurality of reference biosignals received from a plurality of sensors coupled to the test subject, wherein each of the plurality of reference biosignals is assigned with a respective value of a reference parameter, wherein the reference parameter comprises a heart rate, and wherein the values of the reference parameter describe at least partially a physiological state of the test subject and/or a boundary condition of surroundings;
 measuring a control biosignal of the test subject;
 determining a value of the reference parameter assigned with the control biosignal;
 selecting at least one comparative biosignal from the plurality of stored reference biosignals, based on a value of the reference parameter assigned to the control biosignal, and on a plurality of values of the reference parameter assigned to the plurality of reference biosignals;
 comparing the measured control biosignal with the selected comparative biosignal; and
 outputting an action recommendation based on a deviation between the control biosignal and the comparative biosignal,
 wherein the plurality of reference biosignals is provided as a plurality of intervals of a continuous time series.

2. The method according to claim 1, wherein among the plurality of reference biosignals, a reference biosignal having an assigned value of the reference parameter representing a value identical to or having the smallest difference with respect to the value of the reference parameter assigned to the control biosignal, or having an assigned value of the reference parameter representing the next higher or the next lower value with respect to the value of the reference parameter assigned to the control biosignal is selected as the comparative biosignal.

3. The method according to claim 1, wherein the reference parameter comprises a plurality of components.

4. The method according claim 1, wherein the measured control biosignal having an assigned value of the reference parameter is recorded as another plurality of reference biosignals having an assigned value of the reference parameter.

5. The method according claim 1, wherein the biosignal is an electrocardiogram, or the biosignal is an ECG-parameter that can be determined from an electrocardiogram, such as, a QT-time interval, times and/or amplitudes in a QRS-complex, ST-segment, P-wave, R-spike, T-wave, Q-spike, S-spike, U-wave, and zero-line.

6. The method according to claim 1, wherein the reference parameter further comprises one or more of the following:
ECG-parameters that can be determined from an electrocardiogram, blood sugar level, blood pressure, oxygen content in blood, electrolyte levels, body temperature, respiratory rate, minute ventilation;
medication of the test subject, posture of the test subject, current and/or motion state of the test subject up till now, habits of the test subject, particularly occupation, eating habits, frequency of sports activity thereof;
time of day, ambient temperature, air pressure, humidity, season.

7. The method according to claim 1, further comprising, outputting at least one of:
the value of the reference parameter assigned to the control biosignal;
the value of the reference parameter assigned to the selected comparative biosignal;
the control biosignal;
the comparative biosignal;
the deviation between the control biosignal and the comparative biosignal; and
a deviation between the value of the reference parameter assigned to the control biosignal and the value of the reference parameter assigned to the selected comparative biosignal.

8. The method according to claim 1, wherein the biosignal is one of, a blood pressure curve, hemogram, electrocardiogram, electroencephalogram, electromyogram, electroretinogram, record of respiratory gas composition, record of excretion composition.

9. A computer program product that is stored on a computer readable medium and performs the steps of the method of claim 1 using a program code implemented by a computer.

10. A system for monitoring biosignals of a test subject, comprising:
at least one sensor comprising ECG electrodes for measuring a control biosignal of the test subject;
a memory for storing a plurality of reference biosignals of the test subject, wherein each of the plurality of reference biosignals is assigned with a respective value of a reference parameter; and
a controller, wherein the controller is configured to:
determine a value of the reference parameter assigned to the control biosignal,
select at least one comparative biosignal from the plurality of stored reference biosignals, based on the determined value of the reference parameter and on the plurality of values of the reference parameter assigned to the plurality of reference biosignals, and
compare the control biosignal and the comparative biosignal,
wherein the plurality of reference biosignals is provided as a plurality of intervals of a continuous time series.

11. A method for using an electrocardiogram as a comparative electrocardiogram with respect to a control electrocardiogram, the method comprising:
receiving a plurality of reference electrocardiograms as a plurality of intervals of a continuous time series measured by a plurality of ECG electrodes coupled to the torso of a test subject,
wherein the electrocardiogram is selected from the plurality of reference electrocardiograms,
respective values of a reference parameter are assigned to each of the plurality of reference electrocardiograms and the control electrocardiogram,
selection of the electrocardiogram is based on the assigned values of the reference parameter.

* * * * *